(12) United States Patent
Afanasenko et al.

(10) Patent No.: US 6,213,922 B1
(45) Date of Patent: *Apr. 10, 2001

(54) DEVICE FOR TREATMENT OF PATIENTS WITH DISTURBED POSTURE AND MOTOR ACTIVITY

(75) Inventors: Nikolai Ivanovich Afanasenko; Arnold Semenovich Barer; Anatoly Ivanovich Grigoriev; Inesa Benediktovna Kozlovskaya, all of Moscow; Albert Pavlovich Savinov, Moskovskaya; Gai Iliich Severin; Xenia Alexandrovna Semenova, both of Moscow; Viktor Mikhailovich Sinigin; Igor Antonovich Sokolovsky, both of Moskovskaya; Evgeny Petrovich Tikhomirov, Moscow, all of (RU)

(73) Assignee: Ajurveda, Moscow (RU)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/646,213
(22) Filed: May 7, 1996

Related U.S. Application Data

(63) Continuation of application No. 08/196,169, filed as application No. PCT/RU92/00247 on Dec. 18, 1992, now abandoned.

(30) Foreign Application Priority Data

Jan. 31, 1992 (RU) .................................................. 5025647

(51) Int. Cl.[7] .................................................. A63B 21/02
(52) U.S. Cl. .................. 482/124; 482/51; 482/121; 482/122; 482/124; 601/23; 601/33
(58) Field of Search .............................. 482/51, 121, 122, 482/124; 601/23, 33

(56) References Cited

U.S. PATENT DOCUMENTS

| | | | | |
|---|---|---|---|---|
| 420,178 | * | 1/1890 | Yagn | ...................................... 601/23 |
| 807,908 | * | 12/1905 | Bradstreet | .............................. 482/51 |

(List continued on next page.)

FOREIGN PATENT DOCUMENTS

| | | |
|---|---|---|
| 066028 | 12/1982 | (EP) . |
| 2120500 | 8/1972 | (FR) . |

(List continued on next page.)

OTHER PUBLICATIONS

Zhuravlev et al., "Surgical Correction of Posture and Walking in Infantile Cerebral Paralysis," Aiastan Publishers, Yerevan, pp. 90–91, 1986.

Smith & Nephew Don Joy ALP PLUS (Ankle Ligament Protector), Rev. 0495, 1 page.

*Lower Extremity Function and Normal Mechanics* by Justin Wernich and Russell G. Volpe, textbook, pp 1–31, 34–57.

Primary Examiner—Jerome W. Donnelly
(74) Attorney, Agent, or Firm—Kenyon & Kenyon

(57) ABSTRACT

A device for treatment of patients with disturbed posture and motor activity comprises shoulder, pelvic, knee, pedal, elbow, hand, and finger supports (1), all of them being interconnected by fixing elements, which are shaped as elastic tie-members (2) and placed on the surface of the patient's body in antagonistic pairs so as to follow anatomical arrangement of skeletal muscles. Each of the tie-members (2) is connected to two of the supports (1) and comprises an adjuster (3) of its tension, which is interposed between the tie-member (2) and one of the supports (1) through a lock (5).

17 Claims, 1 Drawing Sheet

U.S. PATENT DOCUMENTS

| | | | | |
|---|---|---|---|---|
| 1,618,273 | * | 2/1927 | Davidson | 482/124 |
| 2,097,376 | * | 10/1937 | Marshmann | 482/124 |
| 2,467,943 | * | 4/1949 | Mikell, Jr. | 482/124 |
| 3,162,442 | * | 12/1964 | Karlik | 482/124 |
| 3,295,517 | * | 1/1967 | Stevens | 482/51 |
| 4,910,802 | * | 3/1990 | Malloy | 482/124 |
| 5,186,701 | * | 2/1993 | Wilkinson | 482/124 |
| 5,308,305 | * | 5/1994 | Komney | 482/124 |

FOREIGN PATENT DOCUMENTS

| | | | |
|---|---|---|---|
| 2252836 | | 6/1975 | (FR) . |
| 2298314 | | 8/1976 | (FR) . |
| 2390152 | | 12/1978 | (FR) . |
| 1528483 | | 12/1989 | (SU) . |
| 1556675 | | 4/1990 | (SU) . |
| 1639674 | * | 4/1991 | (SU) ................................. 482/124 |

* cited by examiner

DEVICE FOR TREATMENT OF PATIENTS WITH DISTURBED POSTURE AND MOTOR ACTIVITY

This is a continuation of application Ser. No. 08/196,169 filed on Feb. 15, 1994, now abandoned, which is a 371 of International Application PCT/RU92/00247 filed on Dec. 18, 1992, and which designated the U.S.

TECHNICAL FIELD

The present invention relates generally to devices for nonsurgical (conservation) treatment of the locomotor apparatus (locomotorium) in various neuropathies, and more specifically to a device for treatment of patients with disturbed posture and motor activity.

The invention can find most utility when used for treatment of infantile cerebral paralysis.

The invention is likewise applicable in cerebrovascular accidents involving motor disturbances and traumatic lesions of the spinal cord.

Furthermore, the invention can be applied for correction of patient's posture (attitude), as well as for sports exercises.

BACKGROUND ART

At present the number of neuropathic patients suffering from affection of the locomotor functions becomes immense, while infantile cerebral paralysis, in particular, tends to rise, for a number of reasons, in many countries throughout the world.

Treatment of motor functions in infantile cerebral paralysis patients becomes urgent due to both, the number of patients and imperfection of the treatment method available.

The present state of the medical art knows a number of methods and devices for treatment of patients with disturbed posture and motor activity.

One state-of-the-art method for treatment of patients with disturbed posture and motor activity (cf. "Surgical correction of posture and walking in infantile cerebral paralysis" by A. M. Zhuravlev et al., 1986, Aiastan Publishers, Yerevan, pp. 90–91 (in Russian) is known to comprise stage-by-stage plastering, followed by rigidly fixing the position of the limb and trunk with an altered posture. A disadvantage inherent in said method resides in a restricted motor activity (immobility) of a patient, which might result in amyotrophy, spastic phenomena, and increased hypertensive syndrome due to enhanced pathological muscular synergies.

Furthermore, another disadvantage of said object is a prolonged treatment period, that is, from 4 to 6 months.

One state-of-the-art device for treatment of patients with disturbed posture and motor activity is known (FR, A, 2,120,500) to appear as overalls into which flexible inflatable tubes are inserted to impart rigidity thereto.

A disadvantage inherent in said device is the fact that it is aimed at maintaining the patient's body in a definite position, whereby the field of application of said device is extremely restricted. In addition, said device fails to solve the problem of muscular exercises of a patient, which might lead to profound dysfunction of the muscular system.

Another device for treatment of patients with disturbed posture and motor activity is known (FR, A, 2,252,836) to comprise two blades interposed between the patient's thighs, each of said blades being fixed to a respective thigh, and a mechanical system connected to the blades.

The device under discussion suffers from the disadvantage that it can correct only a wrong position of the thighs, knee joints, and feet. In addition, said device is bulky and therefore its application with therapeutic purposes is very questionable.

One more device for treatment of patients with disturbed posture and motor activity is known (SU, A, 1,528,483) to comprise a thoracic, pelvic, and pedal support, and fixing elements to interconnect the aforesaid supports to one another.

The fixing elements are shaped are telescopic stands interconnecting the pedal supports with the pelvic one and with a bar one of whose ends is rigidly coupled to the pelvic support. The bar carries a roller reciprocatingly mounted thereon and rigidly linked to the thoracic support. Two arms are rigidly connected to the pelvic support, the free ends of said arms being connected to springs movably mounted on the telescopic stands.

With the patient's body in the erect position the roller provides a light reclinating effect produced on the entire vertebral column, while the thoracis support provides rest for the upper trunk portion. With an inclined position of the trunk the roller rides over the bar depending on the angle of inclination so as to assume an optimum position, and the springs impart an effort to the bar. Thus, the weight of the inclined trunk portion is compensated for and the muscular system and vertebral column are released from load.

A disadvantage of the abovesaid device consists in that it is intended for treatment of the vertebral column only by releasing it from load. In addition, use of said device might result in restricted mobility of a patient followed by amyotrophy and affected activity of the antigravity muscles. Above all the treatment process with the use of said device is too prolonged.

DISCLOSURE OF THE INVENTION

It is an essential object of the present invention to provide a physiologically normal stereotype of posture and movements.

The present invention has for its principal object to provide a device for treatment of patients with disturbed posture and motor activity, wherein the fixing elements interconnecting the supports have such a construction that enables the patient's trunk and limbs to be fixed in a position approximating normal physiological parameters, while maintaining a possibility of performing energy-loaded movements by the patient, with the amplitude of said movements characteristic of a given patient.

The foregoing object is accomplished due to the fact that in a device for treatment of patients with disturbed posture and motor activity, comprising pelvic and pedal supports placed on patient's trunk and limbs and interconnected by fixing elements, according to the invention, the fixing elements are shaped as elastic tie-members arranged on the patient's body surface so as to follow anatomical arrangement of the skeletal muscles, each of the tie-members being connected to two supports.

The proposed device is instrumental in fixation of joints in a required position and to establish a moment of force effecting flexion, extension, rotation, adduction, and abduction of the patient's limbs and trunk.

According to a preferred embodiment of the invention, the device comprises additional shoulder, knee, elbow, finger and toe supports.

Such an embodiment of the invention makes it possible to fix practically all the joints of patient's trunk and limbs in a preset position and enables patient to perform energy-loaded movements with amplitudes attainable by a given patient.

It is quite reasonable that the device comprises tension adjusters of the elastic tie-members, each of such adjusters being interposed between the respective tie-member and one of the supports.

Provision of the tension adjusters in the device enables one to vary and individually select the force of action exerted by the tie-members on the musculoskeletal system, thus adding to the efficacy of treatment.

Use of the proposed device makes it possible to utilize functional (active) correlation of the pathological positions of the trunk and limbs instead of static (passive) corrections thereof, rearrange the previous pathelogic stereotype of the posture and movements in the central and peripheral nervous systems, potentiate destruction of the old pathological complex of reflexes that has been established in the course of the disease, and create the new control and conduction system through the intermediary of the defense structures of the brain. In addition, the effect produced by the device on the patient's organism consists in that the correction of the locomotorium and energy loading of movements with the limbs and trunk assuming a new position result in activation of the brain central structures in elaborating a new arrangement of the control system of both, the locomotorium and the motor system of the speech-formation system. Practical application of the proposed device allows for creation of the stereotype of posture and movements closely resembling the physiological one.

BRIEF DESCRIPTION OF THE DRAWINGS

Further objects and advantages of the present invention will be understood from the following detailed description of a specific exemplary embodiment thereof and the accompanying drawings, wherein.

BEST MODE OF CARRYING OUT THE INVENTION

Figures 1, 2, 3:
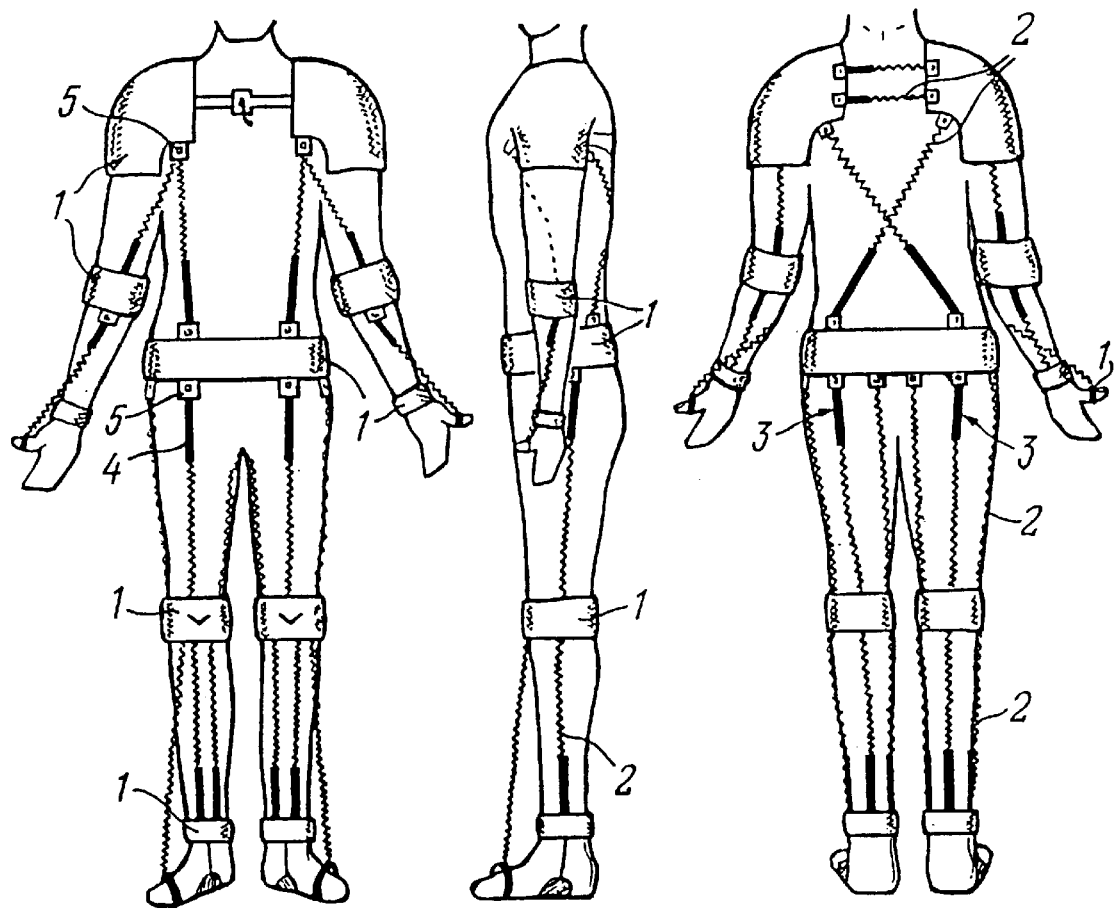
FIG. 1 is a front view of a device, according to the invention.
FIG. 2 is a side view of FIG. 1.
FIG. 3 is a rear view of FIG. 1.

The device of the invention comprises supports 1 adapted for being mounted in the region of the patient's shoulders, elbows, hands, pelvic girdle, knees, feet, fingers, and toes. The supports 1 are interconnected through fixing elements which appear as elastic tie-members 2 adapted to interconnect both the adjacent and nonadjacent supports 1. The tie-member 2 are so connected to the supports 1 that they are arranged on the surface of the patient's body in antagonistic pairs to follow the anatomical arrangement of the skeletal muscles. Each of the tie-members 2 has an adjuster 3 of its tension, which connects said tie-member 2 to one of the supports 1.

Each tension adjuster 3 is in fact a band 4 having one of its ends connected to the tie-member 2 and the opposite end is held to a lock 5 which in turn is fastened on one of the supports 1.

The adjuster 3 may obviously be of any other construction suitable for performing a similar function.

The supports 1 can be made of any material featuring a minimum degree of extensibility, such as fabric, leather, plastics, and so on.

As shown in FIGS. 1, 2, and 3, the supports can substantially cover the joint to which they are mounted. For example, each shoulder support, when properly positioned, can substantially to fully cover the front, top, and back exterior surfaces of its respective shoulder joint, by defining a cup-shaped shoulder harness that contacts, conforms, and covers most, if not all, of the exterior curvilinear skin surfaces of the shoulder. Additionally, the supports can closely surround their respective joints. For example, each knee support, when properly positioned, can closely surround its respective knee, by defining a cuff-shaped knee harness that substantially conforms to the anatomy of the exterior surfaces of the knee by closely contacting, conforming to, and covering most, if not all, of the curvilinear exterior skin surfaces of the knee. Thus, when a load is applied to a given support by any attached tie-member, the load is not transferred to any other tie-member connected to that support.

Specifically, the tie-members 2 can be made of rubber, plastics, or appear as metallic springs.

The device of the invention functions as follows.

The proposed device is selected individually for every patient taking account of his/her state and size of the body. Then the device is put onto the patient and those tie-members 2 are tensioned which correct the position of the body parts to be treated. The tie-members 2 are adjusted for tension with the aid of the adjuster, whereupon the position thus attained is fixed by the locks 5. The tie-members 2 are adjusted until a new position of the trunk and limbs is reestablished, which approximates the normal physiological one and enables the patient to perform movements with an amplitude close to a maximum one for a given patient. The tension of the time-members 2 is increased at least until a load appears in the group of muscle corresponding to a given movement. This done, the device is ready for use.

One end of the band 4 is connected with the respective tie member 2, while the opposite end of the band 4 is secured in the lock 5 installed in one of said supports 1.

When the elastic tie-members are extended, the means for tensioning the elastic tie members (in the form of the band 4) are shortened, i.e. the length of a section between the elastic tie-member 2 and the lock 5 is reduced. The lock is essentially a conventional buckle comprising a square frame such as buckles used in safety belts.

Thus, a dynamic supporting structure (functional corset) is established with the aid of the present device and the patient is prepared for performing movements.

The device is utilized by the patient with due account of his/her status and individual peculiarities daily for a period of up to 12 hours a day, a treatment cycle lasting for 15–30 days.

The tie-members 2 arranged on the surface of the patient's body in antagonistic pairs to follow the anatomical arrangement of the skeletal muscles with respect to the joints provide all kinds of patient's movements in the course of practical application of the device. In the course of treatment the degree of tension of the tie-member 2 is gradually increased. As the patient becomes adapted to the correcting action of the device, the correction force is increased without affecting the sense of comfort with respect to the load applied.

A new stereotype of control of patient's movements is established in the course of treatment. In addition, the patient's physiological status becomes predominant, which results in a reduced amount of pathological muscular synergies and increased extent of motor activity and allows of correcting the patient's posture in the cases unamenable to treatment with other correcting methods.

The present devices can be additionally furnished with overalls put onto patients above the device. The overalls are provided with openings to provide access to the adjusters 3.

EXAMPLE 1

Male patient B. K., 17. Diagnosis: infantile cerebral paralysis. The diagnosis has been established since the six-month age. By the time of treatment with the proposed device the patient had developed paralysis in the form of spastic diplegia. There occurred triple flexion in the lower limbs complicated by contractures in the ankle joints, internal rotation of the thighs, uncompensated body inclination forwards, difficulties in locomotion, phatologic gait; talipes equinovalgus in both feet ("rocking foot"), internal rotation of both arms, and difficult movements of the hands and fingers. The patient's intellect remained unaffected, as well as phrasal speech. There was noticed high level of psychologic motivation for therapeutic rehabilitation. Previously the patient has been treated medicinally and with the aid physiotherapy, as well as by correction with plaster bandages and solid plaster bars. However, the treatment produced but a transient effect.

The patient passed a treatment course with the proposed device for one month, by daily sessions of 2–3 hours.

The load applied was perceived by the patient within the initial seven days of treatment after which the sensation of load disappeared and adaptation ensued. However, within the initial five days the pathological posture of the patient's trunk and limbs reappeared in two hours after load releasing. On the 10th day of treatment a stable result of treatment occurred manifested in complete disappearance of the pathological posture, elimination of flexural disturbances of the lower limbs, improvement in the gait pattern, facilitating forward displacement of the thighs and higher walking pace. After the 10th day of treatment the patient could walk in the erect position. In addition, by the 10th day of treatment there were observed a considerable decreasing of the pronation disturbances in the hands and fingers. The patient was dismissed in 30 days after admission with a considerable improvement of motor and static functions.

What is claimed is:

1. A method for treating patients with disturbed posture and motor activity, said method comprising:
    placing the patient within a device that includes supports located in a region of the patient's shoulders, elbows, hands, fingers, waist, knees, and feet, the device also including elastic tie-members interconnecting the supports, each shoulder support defining a cup-shaped shoulder harness, the device also including and a plurality of adjusters, each adjuster from the plurality of adjusters interposed between one of the elastic tie-members and one of the supports, wherein each of the adjusters is a band having a first end connected to the respective elastic tie-member and a second end held in a lock located on the respective support;
    positioning the shoulder supports to substantially cover the patient's shoulders;
    locating the elastic tie-members on body surfaces of the patient in antagonistic pairs with due account of an anatomical arrangement of the patient's skeletal muscles.

2. The method of claim 1, further comprising
    tensioning the tie-members via an adjuster until a new position of the patient's trunk and limbs is established which approximates the normal physiological position.

3. The method of claim 1, further comprising:
    tensioning the tie-members via an adjuster until a new position of the patient's trunk and limbs is established which approximates the normal physiological position, the adjuster having one end connected to the tie-member and other end connected to a lock that is fastened on one of the supports.

4. The method of claim 1, further comprising:
    performing movements of the patient's limbs with an amplitude close to the maximum amplitude for the patient.

5. The method of claim 1, further comprising:
    tensioning the tie-members associated with a given limb via an adjuster until a new position of the limb is established which approximates the normal physiological position of that limb;
    performing a movement of the limb with an amplitude close to the maximum amplitude for the patient; and
    increasing the tension of the tie-members associated with the limb until a load appears in the group of muscle corresponding to the movement.

6. The method of claim 1 further comprising:
    moving the patient's limbs in accordance with a treatment plan.

7. A device for treatment of patients with disturbed posture and motor activity, said device comprising:
    supports that, in an operative configuration, are located in a region of the patient's shoulders, elbows, hands, fingers, waist, knees, and feet, each of said supports that are located in the region of the patient's shoulders substantially covering the patient's shoulder and defining a cup-shaped shoulder harness;
    elastic tie-members interconnecting said supports and that, in an operative configuration, are placed on a body surface of the patient in antagonistic pairs with due account of an anatomical arrangement of the patient's skeletal muscles; and
    a plurality of adjusters interposed between the elastic tie-members and the respective supports wherein each adjuster from said plurality of adjusters is a band having a first end connected to the respective elastic tie-member and a second end held in a lock located on the respective support.

8. The device of claim 7, wherein each of said supports that is positioned in the region of the patient's knee, in an operative configuration, is positioned to substantially cover the patient's knee.

9. The device of claim 7, wherein each of said supports that is positioned in the region of the patient's knee, in an operative configuration, is positioned to substantially cover and closely surround the patient's knee.

10. The device of claim 7, wherein each of said supports that is positioned in the region of the patient's elbow, in an operative configuration, is positioned to substantially cover the patient's elbow.

11. The device of claim 7, wherein each of said supports that is positioned in the region of the patient's elbow, in an operative configuration, is positioned to substantially cover and closely surround the patient's elbow.

12. The device of claim 7, wherein each of said supports that is positioned in the region of the patient's ankle, in an operative configuration, is positioned to closely surround the patient's ankle.

13. The device of claim 7, wherein each of said supports that is positioned in the region of the patient's wrist, in an operative configuration, is positioned to closely surround the patient's wrist.

14. The device of claim 7, wherein each of said supports that is positioned in the region of the patient's waist, in an operative configuration, is positioned to closely surround the patient's waist.

15. The device of claim 7, wherein each of said supports that is positioned in the region of the patient's hand, in an operative configuration, is positioned to closely surround the patient's hand.

16. A device for treatment of patients with disturbed posture and motor activity, said device comprising:

supports that, in an operative configuration, substantially cover the patient's shoulders, elbows, hands, fingers, waist, knees, and feet, each of said shoulder supports defining a cup-shaped shoulder harness;

a plurality of elastic tie-members that interconnect said supports, each tie-member from said plurality of tie members interconnecting two of said supports, and, in an operative configuration, said plurality of tie-members are placed on a body surface of the patient in antagonistic pairs with due account of an anatomical arrangement of the patient's skeletal muscles; and a plurality of adjusters interposed between the elastic tie-members and the respective supports, each adjuster from said plurality of adjusters including a band having a first end connected to the respective elastic tie-member and a second end held in a lock located on the respective support.

17. The device of claim 16, wherein said supports, in an operative configuration, closely surround the patient's shoulders, elbows, hands, fingers, waist, knees, and feet.

* * * * *

UNITED STATES PATENT AND TRADEMARK OFFICE
CERTIFICATE OF CORRECTION

PATENT NO. : 6,213,922 B1                                        Page 1 of 1
DATED     : April 10, 2001
INVENTOR(S) : Nikolai Afanasenko et al.

It is certified that error appears in the above-identified patent and that said Letters Patent is hereby corrected as shown below:

Column 2,
Line 11, change "are" to -- as --.

Column 3,
Line 50, change "tie-member 2" to -- tie-members 2 --.

Signed and Sealed this

Fourteenth Day of May, 2002

*Attest:*

*Attesting Officer*

JAMES E. ROGAN
*Director of the United States Patent and Trademark Office*